(12) United States Patent
Westerhoff et al.

(10) Patent No.: US 11,688,488 B2
(45) Date of Patent: *Jun. 27, 2023

(54) QUANTUM MECHANICAL/X-RAY CRYSTALLOGRAPHY DIAGNOSTIC FOR PROTEINS

(71) Applicant: QuantumBio Inc., State College, PA (US)

(72) Inventors: Lance Michael Westerhoff, Annville, PA (US); Oleh Y. Borbulevych, Bellefonte, PA (US); Roger Isaac Martin, State College, PA (US)

(73) Assignee: Quantumbio, Inc., State College, PA (US)

( * ) Notice: Subject to any disclaimer, the term of this patent is extended or adjusted under 35 U.S.C. 154(b) by 356 days.

This patent is subject to a terminal disclaimer.

(21) Appl. No.: 16/801,588

(22) Filed: Feb. 26, 2020

(65) Prior Publication Data

US 2020/0194096 A1 Jun. 18, 2020

Related U.S. Application Data

(62) Division of application No. 15/017,453, filed on Feb. 5, 2016, now Pat. No. 10,614,909.

(60) Provisional application No. 62/157,787, filed on May 6, 2015, provisional application No. 62/112,951, filed on Feb. 6, 2015.

(51) Int. Cl.

| | |
|---|---|
| *G01N 33/48* | (2006.01) |
| *G01N 33/50* | (2006.01) |
| *G16B 15/00* | (2019.01) |
| *G16B 20/00* | (2019.01) |
| *G16B 20/30* | (2019.01) |
| *G01N 23/20008* | (2018.01) |
| *G01N 33/68* | (2006.01) |

(52) U.S. Cl.
CPC ....... *G16B 15/00* (2019.02); *G01N 23/20008* (2013.01); *G01N 33/6803* (2013.01); *G16B 20/00* (2019.02); *G16B 20/30* (2019.02); *G01N 2223/304* (2013.01); *G01N 2223/612* (2013.01)

(58) Field of Classification Search
CPC ........ G16B 15/00; G16B 20/00; G16B 20/30; G01N 23/20008; G01N 33/6803; G01N 2223/304; G01N 2223/612
See application file for complete search history.

(56) References Cited

U.S. PATENT DOCUMENTS 10,614,909 B2 * 4/2020 Westerhoff ............. G16B 20/00

OTHER PUBLICATIONS

Borbulevych et al.,Incorporation of the Quantum Chem Pkg DivCon into the PHENIX suite, Acta Cryst, 2011, A67, C593, poster MS58.P06.
Craw et al. Solvation & Solid State Effects of the Structure & Energetics of the Tautomers, Journal of Chemical Physics, 1997, vol. 106, pp. 6612-6617.
Benedetti E.,X-ray Crystallography of Peptides: The Contributions of the Italian Labs. Biopolymers(Peptide Science), V40, pp. 3-44, 1996.
Sanders et al., From the Protein's Perspective: Benefits & Challenges of Protein Structure-based Pharmacophore Modeling, Med. Chem.Commun. V3, pp. 28-38, 2012.

* cited by examiner

*Primary Examiner* — Russell S Negin
(74) *Attorney, Agent, or Firm* — Barbara E. Johnson, Esq.

(57) ABSTRACT

An analytic method for improving the efficiency in identifying protein molecular effect information using low resolution x-ray crystallography, by selecting and imaging a protein sample with low resolution x-ray crystallography and assaying the data thus generated as to local ligand strain energy value, followed by calculating a real-space difference density Z for each element and compiling ZDD data therefrom, followed by determining the true protomer/tautomer state of the protein sample by calculating $Score_i$ according to the following equation so that the highest $Score_i$ signifies the molecular effect information:

$Score_i = \{((ZDD_i - \mu_{ZDD})/\sigma_{ZDD}) + ((SE_i - \sigma_{SE})/\sigma_{SE})\}$.

4 Claims, No Drawings

QUANTUM MECHANICAL/X-RAY CRYSTALLOGRAPHY DIAGNOSTIC FOR PROTEINS

CROSS REFERENCE TO RELATED APPLICATIONS

This patent application claims priority to, and incorporates herein by reference, U.S. Provisional Application for Patent No. 62/157,787 filed 6 May 2015 and U.S. Provisional Application for Patent No. 62/112,951, filed 6 Feb. 2015. This patent application is moreover a divisional patent application of U.S. Ser. No. 15/017,453, filed 5 Feb. 2016.

STATEMENT REGARDING FEDERALLY SPONSORED RESEARCH

This invention was made with government support under Contracts No. R44GM112406 and No. R43GM113555 awarded by The National Institutes of Health of the United States of America. The U.S. Government has certain rights in the invention.

BACKGROUND OF THE INVENTION

Field of the Invention

The invention pertains to identifying real-world conformational, protonation and solvent effects of proteins further to identify binding characteristics between one or more proteins and targets therefore, such as drug molecules or other active agents or ligands.

Description of Related Art

Identifying in advance how a drug molecule will interact with conformations of its target protein or proteins, in vivo, has been challenging up until the present invention. Theoretical models alone are virtually impossible to use, given the unpredictable conformations of proteins or their protonation and solvent effects, that is, the chemical as well as the physical behavior of the protein or proteins in vivo. X-ray crystallography can image a target protein to an extent but cannot provide enough information about epitopes, protonation or solvent effects to confirm details of reactivity with a ligand (drug molecule) of interest. Other tests besides X-ray crystallography, such as without limitation gel- or chemiluminescence-imaging, nuclear magnetic resonance (NMR) imaging or Western Blot testing, give even less structural information than X-ray crystallography does. NMR can "see" protons but is quite limited as to the size and types of structures on can characterize with it. One particular study technique, neutron diffraction, can indeed correctly assess proteins in a sophisticated way, but neutron diffraction is extremely laborious and time-consuming, not to mention costly, and will therefore always be untenable as a method to diagnose real-world protein states in any sort of real-world investigation. Prior to the present technology, therefore, a need persisted for a practical and reliable diagnostic that could assess a real world protein or protein, in vitro or in vivo, to identify all of its conformation, protonation and solvent effects exactly as they behave in real life, further to identify how the protein in fact reacts with a target ligand (drug molecule or other active agent)—not just theoretical projections or models.

SUMMARY OF THE INVENTION

In order to meet this need, the present invention is a diagnostic which bolsters x-ray crystallography with the addition of semi-empirical quantum mechanics analysis to give a verifiable physical and biochemical assessment of a protein or proteins. Even though neutron diffraction is too labor intensive to use on a regular basis for protein testing generally, for the purpose of verifying this invention neutron diffraction has confirmed for three examples that the present quantum mechanical x-ray crystallography diagnostic accurately assesses protein conformation, protonation and solvent effects. Therefore, neutron diffraction has already confirmed that the present tool is a useful and reliable diagnostic of protein structure and reactivity in vivo as well as in vitro. The present quantum mechanical x-ray crystallography diagnostic takes x-ray crystallographic data collected from a protein of interest and overlays (bolsters) the x-ray crystallography with a semi-empirical quantum mechanical set of identification steps as follows, to give a real world diagnostic of the status, conformation and reactivity of the protein in question. Specifically, the overlay in part takes the form of what we call a scoring event. In other words, the present invention includes a novel scoring method, called XModeScore, which (1) enumerates the possible protomeric/tautomeric modes, and thereafter (2) uses X-ray crystallographically to refine each mode specifically by using the semiempirical quantum mechanics (PM6) Hamiltonian, and subsequently (3) we score each mode using a combination of energetic strain (or ligand strain) and rigorous statistical analysis of the difference electron density distribution. By performing these three steps as what we call XModeScore, we are able consistently to distinguish the correct bound protomeric/tautomeric modes based on routine X-ray data—even at x-ray crystallography resolutions that those skilled in the art would consider to be "low." As mentioned above, we have confirmed these bolstered x-ray crystallography results with results obtained from much more expensive and laborious neutron diffraction studies for three different examples: tautomerism in the acetazolamide ligand of human carbonic anhydrase II (PDB 3HS4 and 4K0S); tautomerism in the 8HX ligand of urate oxidase (PDB 4N9S and 4N9M); and protonation states of the catalytic aspartic acid found within the active site of an aspartic protease (PDB 2JJJ). In each case, XModeScore conducted with the X-ray crystallography diffraction data identified the correct protonation state as defined by the neutron diffraction data, thus corroborating the real-world efficacy of the present invention.

DESCRIPTION OF THE PREFERRED EMBODIMENT(S)

Within structure-guided drug discovery (SGDD) and structure-based drug discovery (SBDD), accurate understanding of the protein:ligand complex structure, including the relevant proper protonation, is crucial for obtaining meaningful results from docking/scoring, thermodynamic calculations, active site exploration, lead optimization, and ultimately, medicinal chemistry. The most ubiquitous element in the universe is hydrogen, and these protons are critical for exploring the chemistry within the active site. For example, in the drug Mirapex, which is used to treat symptoms of Parkinson's disease, the important chemical activity is conferred by a single aminothiazole tautomeric state rather than an alternative imino tautomer; thus the selection of the wrong state during the drug design would lead to irrelevant findings. This situation is not uncommon, and drug discovery frequently hinges on the determination of one state vs. another state. The present invention provides a verifiable diagnostic to identify not only structure, protonation and solvent effects in proteins, but specifically also (under that conceptual umbrella) tautomeric state of a protein or proteins.

The most common prior art method for structure determination in SGDD/SBDD is macromolecular X-ray crystallography. Unfortunately, an intrinsic problem of X-ray crystallography is its inability to explicitly detect hydrogen atoms—even at resolutions close to atomic—because the hydrogen atom has the weakest scattering power for X-rays among all elements. Hydrogen atoms are small, and their electrons are shifted towards the heavy atoms to which they are bound. Hence, x-ray crystallography itself is not practical for identifying the protonation or tautomeric state of both the ligand and the surrounding active site. As described above, protonation states can be unambiguously established using neutron diffraction because the neutron scattering length of deuterium is similar to that of heavy atoms. Thus, the scattering by hydrogen/deuterium is comparable to that of other atoms in macromolecular structures. However, the specific limitation of neutron diffraction that limits its practical application is the considerable weakness of the neutron beam, leading to reliance on very large crystals and long exposure time for collection of data of sufficient precision (hence excessive, time, labor and expense). Furthermore, the neutron diffraction experiment requires complete deuteration of the sample crystal, which is difficult to achieve as a practical matter, since exchangeable protons constitute only about ¼ of all hydrogens. Finally, a hydrogen atom has a negative scattering length in contrast to its isotope deuterium D, thus, the presence of hydrogen atoms gives rise to the cancellation effect during the refinement against neutron data, reducing the convergence radius. As a result, neutron diffraction is rarely if ever feasible within industrial SBDD settings.

In addition to the experimental limitations of X-ray crystallography with respect to proton detection, the functionals used in conventional refinement are generally rudimentary in nature and do not account for interactions such as hydrogen bonds, dispersion, electrostatics, polarization and charge transfer. We have therefore developed the present hybrid quantum mechanical x-ray crystallography diagnostic (the combination of XModeScore and x-ray crystallography) in order to overlay powerful quantum mechanics analysis onto the x-ray crystallography data to yield a practical and useful result. As opposed to score functions used in other fields, such as affinity prediction functions used in docking/scoring algorithms, XModeScore "scores" the various protonation modes using X-ray density and thereby provides a real-world, verifiable diagnostic of protein state and binding affinity. This diagnostic is indeed ultimately rendered by a computer as an output to a user, with that output's representing a protein diagnostic that is useful and practical for industrial use and for which there is currently no industrial substitute or competitor (as industrial competitors to the applicants have confirmed).

Validation Method and Structure Selection, Preparation, and Refinement

Neutron diffraction does not suffer from the same deficiencies as X-ray diffraction in regards to proton scattering, suggesting that neutron diffraction can serve as "gold standards" to which X-ray results can be compared. Further, since the XModeScore method is directly dependent upon the X-ray crystal, the current diagnostic is sensitive to the actual protonation state found within that crystal and therefore experimental conditions are important considerations. With this in mind, in order to choose a validation set, we focused on those structures which (a) have both an X-ray diffraction model and a neutron diffraction model; (b) have crystallization conditions (e.g. pH, solvent, temperature, etc.) which are approximately identical between both the X-ray experiment and the neutron experiment; (c) are complexed with chemically relevant or pharmaceutically interesting ligands; and (d) include deposited structure factors. The neutron diffraction model also had to be of a high enough quality that the key protonation states could be determined. Therefore, out of the 88 neutron diffraction structures available in the PDB as of this writing, we chose three:

AZM/human carbonic anhydrase II (HCAII) complex—Neutron: 4G0C, X-ray: 3HS4;
8HX/urate oxidase complex—Neutron: 4N9M, X-ray: 4N9S; and
PD-135,040/aspartic proteinase complex—Neutron: 2VS2, X-ray: 2JJJ.

A second HCAII X-ray model, 4K0S, was also selected in order to demonstrate the impact of x-ray crystallography resolution on XModeScore results and, by extension, the present.

The X-ray structures along with their structure factors were downloaded from the Protein Database (PDB). Hydrogen atoms were added to protein residues, water molecules, and ligands using Protonate3D as implemented in MOE2013 from Chemical Computing Group, Inc. Foreseeable protomer/tautomer states were automatically generated with MOE2013 using the WashMoleculeMOE Scientific Vector Language (SVL) function. Since Protonate3D settles on a single protomeric/tautomeric state, after execution of WashMoleculeMOE, each candidate protomeric/tautomeric state was fixed and Protonate3D was re-executed on the structure in order to "propagate" proton addition/subtraction (along with corresponding residue rotameric flips) based upon each tautomer or protomer. In this way, protons are added/changed within the active site to match or counterbalance H-bond changes within the ligand. The QM region refinement was conducted on each structure using libQB (DivCon/build-2577) incorporated into the Phenix package version 1.9-1692. The PM6 semiempirical, QM Hamiltonian was used for each QM region, where each QM region was centered around the ligand AZM in PDBs 3HS4 and 4K0S, the ligand 8HX in PDB 4N9S, and the key catalytic residue Asp215 in PDB 2JJJ. For the region refinement, the default radii of 3.0 Å and 2.5 Å for the main and buffer regions respectively were used. To explore the impact of resolution on each refinement and score, each structure was refined at several levels of dataset truncation using the phenix.refine keyword 'xray_data.high_resolution=X,' where X refers to the desired high resolution cutoff in Å.

In addition to QM-based X-ray refinement, conventional (i.e. non-QM) refinements for each case were also performed in order to explore the impact of refinement method on XModeScore results. In each refinement, the same version of Phenix was used for refinement and its electronic Ligand Builder and Optimization Workbench (eLBOW) module—using the AM1 Hamiltonian—was used to generate the CIF files for the same set of tautomers generated for QM-based refinement.

XModeScore: Scoring Procedure.

The overall goal of XModeScore is to determine which protonation or tautomer form is found in the experimental structure. After the refinement, each structure was scored based on a combination of metrics which take into account both structural characteristics of the ligand, and its fit within the active site, as well as the quality indicators of its agreement with crystallographic electron density. The local ligand strain energy (SE) serves as an important quality indicator of protein-ligand structures because it shows how much strain the ligand must accept to bind with the protein. The SE or $E_{Strain}$ is defined as the difference between the energy of the isolated ligand conformation and the protein-bound ligand conformation and is computed according to the equation (1), $$E_{Strain} = E_{SinglePoint} - E_{Optimized} \tag{1}$$

where $E_{SinglePoint}$ is the single-point energy computed for the ligand X-ray geometry, and $E_{Optimized}$ is the energy of the optimized ligand that corresponds to the local minimum.

The experimental quality indicator component of XModeScore is a measure of the diagnostic accuracy. The generally accepted quality metric of the X-ray electron (or neutron) density is the Real Space Correlation Coefficient (RSCC). The RSCC reflects the degree of correspondence between the experimental (observed) and calculated electron densities. However, RSCC correlates both with accuracy and with precision of the diagnostic, and it is not possible to say to what extent RSCC reflects the accuracy of a given model due to the variable contribution from the precision component. On the other hand, the real-space difference density Z score for a point difference density value defined in equation (2) provides a more sophisticated quality indicator since it measures the accuracy of the diagnostic, $$Z[\Delta\rho(r)] = \frac{\Delta\rho(r)}{\sigma[\Delta\rho(r)]}, \tag{2}$$

where $\Delta\rho(r)$ is the difference density at the coordinate vector r expressed as the real Fourier transform (3).

$$\Delta\rho(r) = \tag{3}$$
$$(2/V_{cell})\sum_h c(h)[m(h)F_{obs}(h) - D(h)F_{calc}(h)] \times \cos[2\pi r \cdot s(h) - \varphi(h)].$$

Here, the sum is over observed reflections with index vector h symmetry-expanded to a complete hemisphere in reciprocal space, $F_{obs}(h)$ and $F_{calc}(h)$ are the observed and calculated structure amplitudes respectively, $\varphi(h)$ is the phase calculated from the diagnostic, c(h) is the centricity factor (1 for centric reflections or 2 for acentric), m(h) is the expected cosine of the phase error, D(h) is a correction factor for errors in the diagnostic, and s(h) is the scattering vector.

In equation (2), $\sigma\{\Delta\rho(r)\}$ is the standard deviation of the difference density, which is the standard measure of random error and is therefore a pure precision metric. The Z score of the difference density is a measure of the residual non-random error, so is a pure accuracy metric. However, a single minimum or maximum value of the difference density might not be statistically sound, as it is easy to over-interpret the significance of such a Z score. Different density Z values should approach a normal distribution of random errors with zero mean and unit standard deviation as the quality of the model improves, and the presence of significant positive or negative peak outliers that deviate from the expected distribution indicate problems with the model. Therefore, rather than using the point density at the atom center, or a single minimum or maximum value for each atom taken over all grid points covering the atom, it is more reliable to compute the standard chi-square ($\chi^2$) statistic for a subset of the absolute negative values, and similarly for the positive values, of the density at the grid points covering an atom, assuming independent and identically distributed (iid) random variables. In each case the selected subset starts at the $k^{th}$ value in increasing order of magnitude (4), $$\chi_k^2 = \sum_{i=k}^{N} x_{(i)}^2 \tag{4}$$

where $x_{(i)}$ is the $i^{th}$ normal order statistic (i.e. postulating the null hypothesis of a normal distribution) of the $|Z(\Delta\rho)|$ scores for the negative and positive values respectively (i.e. in each case the $i^{th}$ value after sorting each array of $|Z(\Delta\rho)|$ values in increasing order of magnitude).

Thus, all such grid point density values become potentially relevant during the evaluation of the ZDD metric. Clearly, we do not know a priori which of the density values are significant: if we choose too few, we may lose information, but if we choose too many and add noise then $\chi^2$ will lose significance. Therefore, it is reasonable to sum only the subset of values of $x^2_{(i)}$ that maximizes the probability $p_{max}$ over k, $$p_{max} = \max_k P\left(X_k^2 \leq \sum_{i=k}^{N} x_{(i)}^2\right) \approx \tag{5}$$
$$\max_k P\left[1/2\sum_{i=k}^{N} x_{(i)}^2; (N+1-k)/2\right] \times I\{2\Phi[x_{(k)}] - 1; k-1, N+1-k\},$$

where the function P is the lower normalized gamma function representing the cumulative distribution function (CDF) of $\chi^2_k$. In practice, the CDF is computed as the complement (1−P) to avoid problems with numerical precision for values of the function P near unity i.e. the most relevant values for present purposes. The second function, I, which is also computed as the complement in practice, is the normalized incomplete beta function (CDF of a normal order statistic) which accounts for the 'multiple comparisons' correction. It is worth remarking that in the special case of k=N, where the maximal probability $p_{max}$ occurs when only the single maximum absolute density value is used, the function I becomes the Dunn-Šidák correction. Another special case occurs for k=1 where the maximal probability occurs when all density values are used. In this case there is no 'multiple comparisons' correction so then the function I is exactly 1 and the combined function reduces to the CDF of $\chi^2$ for N degrees of freedom, as expected. In this way, the probability $p_{max}$ makes no assumptions about the spatial distribution of significant grid point values in the vicinity of an atom (e.g. whether there is a single sharp maximum, or a broad maximum, or multiple maxima). Rather, the value of $p_{max}$ adapts to the actual distribution and attempts to quantify the probability that the distribution of grid point values could not have arisen purely from random variations.

ZDD is evaluated as the two-tailed normal Z score corresponding to the maximal value $p_{max}$ over k of the cumulative probability of $\chi^2_k$ derived from (4) and (5).

$$ZDD = \Phi^{-1}((1+p_{max})/2) \tag{6a}$$

or $$ZDD = -\Phi^{-1}((1-p_{max})/2) \tag{6b}$$

Here, the function $\Phi$ is the CDF of the normal distribution (so $2\Phi(|Z|)-1$ is the CDF of the half-normal distribution of the absolute value of a normal variate Z), and $\Phi^{-1}$ is the inverse function (i.e. the value of Z corresponding to a given probability). The form (6b) is preferred, because the complement $(1-p_{max})$ of the probability was calculated in the previous step.

ZDD also depends on the radius $r_{max}$ enclosing the atomic density grid points; this is determined from the radius integral (7):

$$R_{atom} = \int_0^{r_{max}} \rho(r)dr. \quad (7)$$

The radius $r_{max}$ corresponds to the value of the radius integral $R_{atom}$ that is 95% of the theoretical value at infinite radius. For this purpose, the calculated atomic density function $\rho(r)$ is determined from the spherically-averaged real Fourier transform according to (8), $$\rho(r) = \left(\frac{8n}{r}\right)\int_{s_{min}}^{s_{max}} f(s)\exp(-Bs^2)\sin(4\pi rs)s\,ds, \quad (8)$$

where n is the fractional occupancy of the atom, $$s_{min} = \frac{0.5}{d_{max}}$$

depends on the maximum d-spacing (or low resolution limit)

$$d_{max}, s_{min} = \frac{0.5}{d_{max}}$$

similarly on the minimum d-spacing (or high resolution limit) $d_{min}$, f(s) is the atomic scattering factor for X-rays as a function of s, and B is the isotropic displacement parameter (B factor). Thus the width of the atomic density function (and hence $r_{max}$) will be greater at lower resolution and for larger values of the B factor, in line with what one expects to see in an electron (or neutron) density map. Where the densities of adjacent (i.e. bonded) atoms overlap the densities at the grid points in the electron density map are partitioned in proportion to the atomic densities calculated from eq. (8).

To avoid oversampling the density values at the grid points, which would invalidate the iid assumption made above, the set of density values are resampled according to the Shannon-Nyquist theorem. This theorem states that the density values at the grid points are statistically independent when the sampling interval is at least $d_{min}/2$, where $d_{min}$ is the minimum d-spacing of the data used in the computation of the map. Typically, maps are sampled at an interval of not more than $d_{min}/4$ for accurate interpolation and to avoid missing important features, so the map would need to be resampled for the statistical calculations at about every $2^{nd}$ grid point in each direction. However, since resampling the map in 3 dimensions might lose information such as significant outliers, the density values are sorted by increasing value as a 1-dimensional array and then resampled, keeping only a fraction (e.g. ⅛).

The set of negative density values then yields a metric that we call 'ZDD−', and the set of the positive densities yields the metric 'ZDD+'. Therefore, the effects of negative difference density, due to incorrectly positioned atoms, and positive difference density (perhaps due to an incorrectly typed atom) can be separately identified. The ZDD− and ZDD+ metrics are also taken together to give a final combined ZDD metric defined as (9).

$$ZDD = \max(ZDD-, ZDD+) \quad (9)$$

The lowest ZDD in the series of ligand tautomeric forms allows us to choose the best form or protonation state that demonstrates the closest match with experimental density. Then, with both QM-SE and ZDD in hand, the overall score of the i-tautomer form can be calculated according to (10), $$Score_i = -\left(\frac{ZDD_i - \mu_{ZDD}}{\sigma_{ZDD}} + \frac{SE_i - \mu_{SE}}{\sigma_{SE}}\right), \quad (10)$$

where $\mu$ is the mean value and $\sigma$ is the standard deviation of the corresponding array of data (ZDD or SE). For example, the SE array contains SE values for all tautomers included in the calculations. The highest $Score_i$ corresponds to the best tautomeric form 'i' that fits both SE and ZDD criteria.

Results

The Protonation State of AZM Bound to Human Carbonic Anhydrase II: PDB 3HS4 at 1.1 Å Resolution.

Human carbonic anhydrase II (HCA II), which catalyzes hydration/dehydration of carbonates, is involved in numerous metabolic processes including $CO_2$ transport and pH regulation and is therefore considered an important target for drug design. The drug acetazolamide (AZM), sold under the name "Diamox," is a high affinity inhibitor of HCA II that is efficiently used to treat a number of medical conditions such as altitude illness, hypertension, and glaucoma. It binds to the Zn atom of the enzyme via the nitrogen atom of the sulfonamido group. Zn is located in the catalytic center of HCA II and adopts a tetrahedral coordination, making coordination bonds with nitrogen atoms of His94, His96, and His119. AZM can exist in several tautomeric forms, which are depicted in Scheme 1 below. However, even high resolution X-ray diffraction studies failed to determine which form of AZM is actually involved in the enzyme interaction. Conventional protonation determination methods, such as the analysis of the bond length distribution, also failed in the case of AZM. It was only with the recent neutron diffraction study that it was established that AZM exists in form 3, which includes the negatively charged sulfonamido $SO_2NH$ group bound to zinc.

Scheme 1. Possible binding modes of the drug AZM.

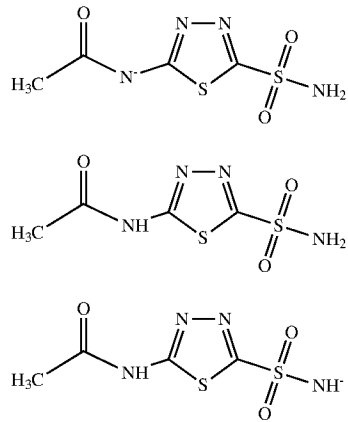

Scheme 1. Possible Binding Modes of the Drug AZM.

We challenged XModeScore on the three structures which include three possible forms of AZM beginning with PDBid: 3HS4 (Table 1). The results indicate that form 3—the correct protonation state according to the neutron diffraction experiment—is indeed the superior form, dominating in both components of scoring. There is a significant difference in the score for form 3 (2.72) and the score for the second best option (−0.74), which corresponds to form 2. It is important to note that the ZDD of form 3 is almost half that of the other two forms, which suggests that structure of the tautomer 3, with the negative charge on the nitrogen atom N1 bound to zinc, is more consistent with the experimental structure amplitudes than are the forms with the amino group at this position. The difference density maps obtained after the QM refinement show that the negatively charged N1 plays a crucial role in binding to HCA II. In particular, large negative/positive peaks of the difference density are seen around the nitrogen atom N1 for the tautomers 1 and 2 and effectively explains the larger magnitude of ZDD observed for the former tautomer states as compared to form 3. Furthermore, the analysis of the bond length distribution around zinc after the QM refinement (Table 2) has shown that the bond Zn—N1$^{AZM}$ in tautomer 3 (1.90 Å) is much shorter than the length of that coordination bond in the other two tautomers (2.05 and 2.07 Å) and also shorter than the average length of 2.00 (2) Å for the Zn—N bond type. Nevertheless, such a binding geometry of the ligand AZM with the shortened Zn—N1 bond seen in form 3 agrees much better with the experimental data. Specifically, the atomic ZDD for the atom N1 in the form 3 is four fold lower than the corresponding values observed for the tautomers with the Zn—NH$_2$ bond.

Effect of the Resolution Truncation on the Predictability of the Tautomer XModeScore.

Generally, at lower resolution, less detail about the crystal model is revealed from experimental data and these experimental data are less sensitive to the model nuances. Hence, the resolution of data sets may affect not only the absolute values of ZDD but also the difference in tautomer scores. The latter is crucial as it determines the ability to distinguish the top tautomeric form from the rest of the candidates in XModeScore. To determine how the resolution affects the predictability of XModeScore, we carried out stepwise truncation of the original data set 3HS4, followed by repetition of the scoring protocol at each resolution level.

Through the truncation of the original high-resolution data set 3HS4, one can explore how well the method maintains its predictive power over decreasing resolution (Table 1) while controlling for inconsistencies in experimental conditions (pH, temperature, solvent, and so on) between native high and low resolution structures. For the 3HS4 refinement, XModeScore is able to remain predictive until the low resolution of 3.0 Å is achieved. The ΔZDD is the change in ZDD between one tautomer and another tautomer and is an indication of how well the ZDD will differentiate between the tautomers. At resolutions higher than 1.8 Å, tautomer 2 exhibits a high value of ΔZDD. However, ΔZDD falls towards the zero when the resolution decreases to 3.0 Å as molecular details of the structure are becoming smeared as argued above. At the resolution 2.8 Å, ΔZDD is close to zero, which prevents a reliable distinction between the forms 2 and 3 based on the density score alone. Generally speaking, ZDD tends to diminish in magnitude and equalize between tautomers at lower resolutions. On the other hand, when considering the overall ΔScore of XModeScore, the value changes far less and is fairly flat suggesting that even if the experimental density deteriorates with the resolution, the second component (e.g. ligand strain) significantly augments the deteriorating ΔZDD value, and leads to selection of the correct tautomer form at lower resolutions. It is notable that the ΔRSCC function line is the flat, virtually zero line. This relationship underscores the fact that RSCC undergoes very little change between modes. This observation is consistent with the conclusion above that RSCC is not likely an appropriate metric for scoring.

AZM in PDB 4K0S at 1.8 Å Resolution.

While using truncated data is an expedient and straight forward method of exploring predictability, a truncated high resolution dataset still has much better quality in terms of the merging R$_{merge}$ factor of diffraction data, their completeness and redundancy, and as the mean signal-to-noise (I/σ) ratio when compared to those of the native low resolution data. Therefore, we repeated our study on another structure of HCA-II complexed with AZM (PDB 4K0S) determined at the more modest resolution of 1.8 Å. Again, just as in the 3HS4 case, XModeScore found that tautomer 3 is the preferable one according to both ZDD and SE components (Supplementary Table 1).

The 8HX Inhibitor in PDB 4N9S

The enzyme urate oxidase is involved in the metabolism of purines, and to investigate the mechanism of action of urate oxidase, the neutron diffraction structure of the enzyme in complex with uric acid monoanion (the inhibitor 8HX) was determined (PDB 4N9M). In particular, the inhibitor is present in the form of 8-hydroxyxanthine monoanion 24 that exists in equilibrium with the form 21 in solution (Scheme 2).

Scheme 2. The key lactam-lactim equilibrium for the ligand 8HX.

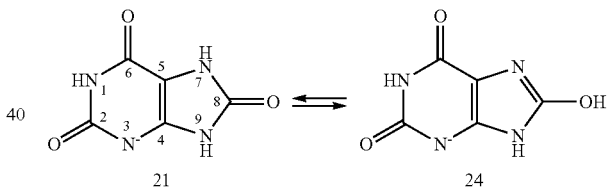

The neutron diffraction structure 4N9M has revealed that the form 24 occurs in the crystal form. Such a conclusion is supported by an unambiguous deuterium density peak near the oxygen at the position 8 reflecting the hydroxyl group. The authors postulate that there is a water molecule near the hydroxyl O(7)H observed in the neutron diffraction experiment that might stabilize form 24. However, a water molecule is capable of being both a donor and an acceptor of H-bonds, and it is more likely to adapt to the solute (protein:ligand complex) rather than decisively determine its protonation state (Krieger et al., 2012). Since this water molecule is not seen in the relevant high resolution X-ray structure 4N9S, we believe that the H-bond between N7 of the ligand and N—H (backbone) of Thr57 observed with the symmetry-related protein molecule in the crystal favors unprotonated N7 and hence the tautomer 24.

As many as 30 tautomer/protonation candidates of 8HX were generated by WashMoleculeMOE (Supplementary Scheme 1), and XModeScore scores tautomer 24 at the top of the list based upon both scoring components (Supplementary Table 2). Comparing 24 (Score 3.87) with its counterpart 21 (Score 1.14) in the equilibrium shows the clear preference of the former. Additionally, the ZDD for 24 is lower (better) than the ZDD of 21 by 3.2 units. Truncating the resolution of the data, followed by QM refinement of the same set of tautomer structures, generally shows a similar trend until the low resolution 3.0 Å is reached: the tautomer 24 remains on the top of the list while the form 17 is consistently at the bottom (Supplementary Table 2).

The Protonation State of the Catalytic Asp215 in 2JJJ.

Aspartic proteinases are enzymes involved in many metabolic processes and are associated with the progression of a number of diseases including AIDS, and in recent years, aspartic proteinases have received significant attention as promising drug design targets. Several crystal structures of aspartic proteinases with a number of inhibitors are known, including the inhibitor PD-135,040 (PDB ligand 0QS) (Supplementary Scheme 2), for which a neutron diffraction study has also been conducted. The preliminary X-ray study demonstrated that the diol group of the ligand makes strong H-bonds with two catalytic residues of the enzyme: Asp32 and Asp 215. The neutron diffraction model has revealed that the outer oxygen of Asp215 is protonated (structure 1 on Scheme 3).

For this case study, we generated the alternative structure 2 that has Asp215 protonated at the inner oxygen, as well as structure 3 with the fully-deprotonated Asp215 (Scheme 3). The XModeScore results for forms 1-3, after the QM region refinement against the high resolution X-ray structure 2JJJ (Table 3) demonstrate an interesting interplay between the SE strain and ZDD components used within XModeScore. In this case, the SE strain of Asp215 rather than the ligand is considered as we vary the protonation states of the amino acid. In particular, the protonation form 2 has the lowest strain energy, while the strain energy of the correct form 1 is about 3 kcal higher. Nevertheless, the protonation form 1 of Asp 215 is correctly scored as the best form due to markedly better ZDD values. Such a low ZDD of the form 1 can be primarily attributed to positioning of the carboxyl group of Asp 215 that is in much better agreement with experimental structure amplitudes compared to the other two protonation states. Indeed, difference density peaks around the carboxyl group are much lower for the state 1. The location of the atom OD2$^{Asp215}$ is particularly important. Its atomic ZDD in the binding mode 1 is about 4-fold better than that for the states 2 and 3 (Table 4). The superimpositions of the atomic coordinates of Asp215 in all three forms after the QM refinement has revealed that OD2 in 1 is located in between the positions of this atom in the structures 2 and 3 that is also strongly correlative with the distance OD2$^{Asp215}$-F2$^{0QS}$. Indeed, while the separation between the fluorine atom of the inhibitor and the OD2$^{Asp215}$ in 1 is 2.88 Å, the same distance is greater for the form 3 by 0.14 Å but shorter for the state 2 by 0.14 Å (Table 4). Thus, the protonated atom OD2 in 1 apparently adopts an optimal location and even a relatively small shift such as 0.14 Å in any direction seen in 2 and 3 leads to a dramatic increase of the atomic ZDD due to increasing the disagreement with the experimental density (Table 4).

At resolution truncations below 2.0 Å, ZDD scores of the form 1 and 3 become similar. However, form 1 remains the top structure because its strain energy is lower than that of the unprotonated Asp215 form 3. When the data is truncated, this relationship is maintained until the resolution 2.8 Å is reached and the scoring model no longer predicts the correct structure 1.

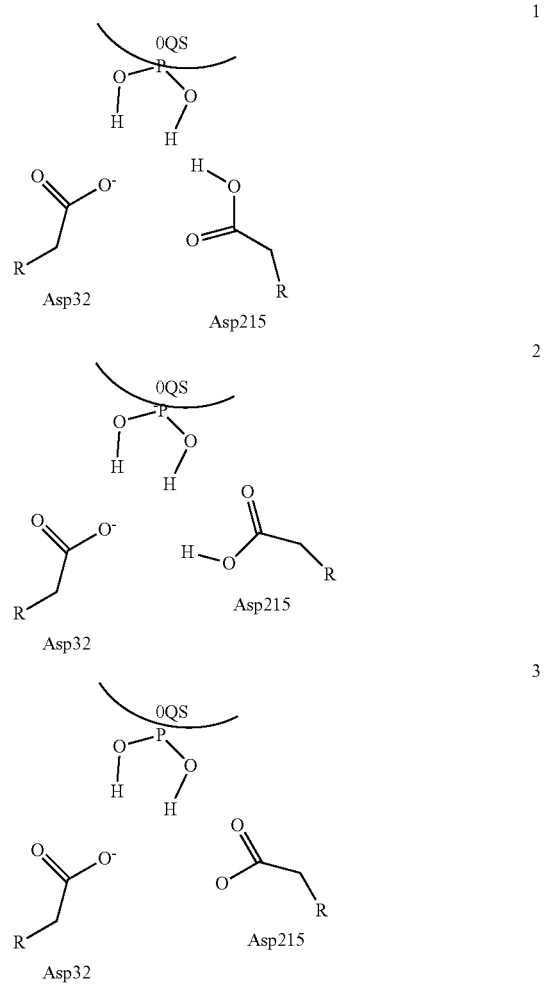

Scheme 3. Three possible protonation states of Asp215 in the structure PD-135,040/Aspartic proteinase.

Discussion

In order to properly guide SBDD efforts, it is crucial to identify the correct tautomer/protomer state of the molecule in the bound state. The building blocks of common drug and drug candidate small molecules include 5,6-membered heterocycles and various functional groups that make possible proton migration from one part of the molecule to another. Prototropy or proton shift tautomerism represents the most common type of molecular rearrangement relevant to SBDD. Keto-enol, imine-enamine and other equilibrium types lead to hydrogen transfer between hydrogen donor groups (e.g. —OH, —NH$_2$) and hydrogen acceptor atoms (e.g. =O, =N—). While the tautomerism changes neither the molecular formula nor the molecular charge, each tautomer is a distinct chemical structure with unique physico-chemical properties. The key point is that different tautomers exist in an equilibrium in solution where the ratio between possible states is affected by pH, temperature, concentration, ionic strength and other factors. The general view is that protein receptors are capable of selectively binding a certain tautomeric form or forms from the mixture of several possible states. For example, the antibiotic tetracycline can exist and react in one of 64 possible tautomeric forms adapting to various chemical environments. A growing body of evidence indicates that sometimes an unexpected tautomer form, or the form which does not correspond to the energy minimum of the tautomer set in vacuum, is found to react with the protein receptor.

The limitations of the current experimental techniques used for structure determination make it difficult to determine these states where even at the extremely high resolution of 0.66 Å, only 54% of all H— atoms are revealed. As an alternative to X-ray crystallography, neutron diffraction is considered to be a unique technique that allows for experimental determination of hydrogen positions in crystal structures at resolutions much lower than those used to reveal atomic details. However, due to the limitations of neutron diffraction such as a reliance on large crystals, the necessity of deuterium exchange, the limited availability of sources of neutron radiation and difficulties in the refinement of hydrogen atoms with negative scattering length, neutron diffraction is of only limited utility in SBDD. In fact, it is notable that as of June 2015, the overall number of structures determined using neutron diffraction available in the PDB remains at 83 vs the total of 97,297 X-ray structures.

We have found that XModeScore is able to determine the protonation state of ligands and catalytic residues using routine X-ray crystallographic data with a level of accuracy only achieved in neutron diffraction studies coupled with high resolution X-ray structures. Even when XModeScore is challenged with truncated or low resolution (e.g. 2.5-3.0 Å) X-ray data, it is still observed to be predictive. The XModeScore method involves the QM X-ray refinement of a set of macromolecular structures containing all likely tautomer/protomer forms or binding modes, followed by a rigorous statistical analysis of difference electron density maps around each candidate form coupled with computation of its QM strain. This approach allows us to choose the best tautomer based on a combination of energetics and of agreement between model and experimental density. After each refinement, the relative stabilities of those protonation states were evaluated from thermodynamic cycles using energies from additional single-point semiempirical DivCon calculations. The key advantage of XModeScore is it directly employs the experimental electron density to judge the bound protomer.

In order to validate the applicability of XModeScore in the present work, we considered several key case studies. For the first example, for many years the correct binding form of the drug acetazolamide (AZM) in human carbonic anhydrase II was uncertain and the correct form was only unambiguously established by the rigorous joint neutron diffraction/X-ray study in 2012. With XModeScore, the same conclusion was reached utilizing the X-ray data alone and it chose the correct tautomeric form over two other possible states of AZM by a wide margin (Table 1). At a structural level, the difference between the correct form 3 and the incorrect binding modes is primarily attributed to shortening the Zn—N coordination bond between the nitrogen of the AZM sulfonamido group and the cofactor of the enzyme seen in the structure 3 (Table 2) after the QM refinement. Notably, the Zn—N distance 1.9 Å in 3 is shorter than the average distance of 2.00 Å for the Zn—N bond type that is typically used for link restraint parameters in conventional refinement, suggesting that without a priori knowledge of the correct outcome, conventional restraint-based refinement would be unable to come to the same conclusion. Nevertheless, such a short Zn—N distance gives rise to the best agreement with the experimental data observed for the binding mode 3 (Tables 1 and 2). This example underscores the importance of the QM refinement as the indispensable step in successful scoring of the tautomer/protomer set. The key and unique advantage of the QM refinement is to derive the geometry of protein-ligand systems objectively without making any a priori assumptions in the form of CIF dictionaries, fixed atom types, link restraints, coordination sphere parameters, or other "user supplied" characteristics. When considering the conventional refinement (Supplementary Table 3), for 3HS4 mode 3 is still shown to be the best structure, however the greater sensitivity of the QM-based refinement is apparent when one considers the standard deviations (SDs) of the ZDD values and the XModeScore values across the three modes. In each case, the SD—or the "spread" of these indicators is much higher for the QM-based refinement. This is a crucial difference with scoring based on the QM refinement which demonstrates that QM-based refinement is better able to discriminate the correct mode 3 by the wide margin in both ZDD and XModeScore as was discussed above. One could speculate that this result could be due to the fact that while the eLBOW-generated CIFile for each tautomer captures the intra-molecular conformational changes associated with protonation states changes, since the intra-molecular interactions (e.g. electrostatics, polarization, charge transfer, and so on) are not captured in the conventional refinement functional, that any impacts of the active site on the different ligand protonation states are likewise missing. It is further notable that the ligand strain energies are an order of magnitude higher for the conventional refinement versus the QM refinement reinforcing the conclusion that the QM refinement is the more robust method.

A large proportion of the neutron diffraction experiments available are focused on studies of enzymatic mechanisms in order to establish protonation states and the H-bond network within the enzyme catalytic center. The aspartic proteinase case study (Tables 3 and 4 and Scheme 3) clearly demonstrates that XModeScore is able to efficiently investigate the protonation state of the key catalytic residue Asp215 using X-ray data alone, and ultimately select the state which corresponds to the one found in the neutron diffraction study reported by Coates et al. In this case, we discovered that there is a strong correlation between the distance $OD2^{Asp215}$-$F2^{0QS}$ and the size of the difference density peaks or the magnitude of ZDD around the atom $OD2^{Asp215}$ (Table 4). A recent review in *Science* underscores the importance of fluorine substituents in SBDD since fluorine has unique properties which impact ligand affinity due to polar hydrophobicity. The ability of fluorine to modulate ligand binding and even the immune response in peptide-based immunotherapy is well documented. Coates et al. do not elaborate on the possible fluorine effect in their manuscript; however, our results suggest that the protonation of Asp215 in the structure with the inhibitor 0QS (PD-135,040) might be modulated by the neighboring fluorine atom rather than generally represent the mechanism of action of aspartic proteinase. Again, as in the AZM case, when considering the conventional refinement results provided, the "spread" or standard deviation of the XModeScores and ZDD scores of the three ASP215 tautomers is an order of magnitude greater and the residue structural strain values are an order of magnitude lower for the QM-based refined models suggesting that the QM values are likely more robust. That said, it is interesting to note that the ZDD of mode 1 is lower (better) than the ZDD of mode 1 observed in the QM-based refinement. Upon further exploration, the elevated ZDD score is associated with backbone O and C atoms of ASP215 which can be attributed to the fact that SE methods such as PM6 overestimate the lengths of some protein backbone bonds.

In the case study of the urate anion (ligand 8HX), XModeScore, using QM-based refinement, is able to select the correct tautomer out of a large number of possible states using the very wide range of data resolution between 1.0-3.0 Å. Given the large number of possible tautomeric forms, it is interesting to consider the pKa of the structure. Uric acid has two pKa (5.4 and 9.8) that are relevant at the physiological pH range considered. As a result, this compound exists predominantly as a monoanionic form. However, this monoanion can undergo lactam-lactim tautomerism shown on Scheme 2 and it can exist in a number of other anionic tautomeric forms (Supplementary Scheme 1). Therefore, the pKa values alone do not allow us to determine the correct tautomer form because all tautomers have the same number of hydrogens and the same molecular charge. When considering the conventional refinement, shown in Supplementary Table 4, while the large number of possible tautomers did allow the conventional refinement to yield ZDD and XModeScores with comparable standard deviations, the conventional refinement was unable to determine the correct tautomer.

CONCLUSIONS

With the calculations performed to date involving protomer/tautomer state determination, XModeScore has shown itself to be versatile and robust. Further, while the method could be used with either QM-based refinement or conventional refinement, clearly the significance of the QM-based results appears to be higher than that observed in the conventional refinement. Another related area of interest is in the exploration of heavy-atom flip state ambiguity often observed in macromolecular X-ray crystallography. X-ray studies of protein-ligand complexes reliably reveal only the configuration of heavy atoms of the structure with the caveat that elements with similar atomic numbers—such as N and O—are often indistinguishable at modest resolutions. This leads to ambiguous orientations of molecule fragments capable for flipping such as imidazole rings, amide groups, and so on. Serious challenges in assigning the correct ligand orientation/flipping in X-ray macromolecular crystallography are well-documented and recognized. Often, the hypothetical flip state is chosen based upon its agreement with the hydrogen bond network and van der Waals contacts with the residue in question. Not only does our method offer an entirely new X-ray data-driven approach for selecting flip states, broadly speaking, any docking/placement of a ligand within the identified locus of electron density can be addressed using our method, to generate real-world and objectively verifiable results.

The invention is susceptible of adjustment and modification without departing from the scope intended. For example, the use of Protonate3D from MOE is exemplary prior technology suitable, by no means exclusively, for adding hydrogens and generating foreseeable protomer/tautomer states, and other tools besides Protonate3D may be used (indeed the applicant is nearly completed with its own work on such a replacement tool). Similarly, QM region refinement does not necessarily have to be conducted with tools incorporated into a Phenix version, but can be accomplished with equivalent tools able to deploy the semiempirical QM Hamiltonian discussed herein. In fact, and regarding the semi-empirical Hamiltonian, it is not only possible to use different Hamiltonians than disclosed above, really any semi-empirical quantum mechanical analysis method (tool) works with the present invention, as would a known ab initio quantum mechanical tool. Having said that, molecular mechanics approaches can also be substituted for quantum mechanical tools to achieve the same surprisingly improved results. While the preferred embodiment of the invention is therefore the use of a semi-empirical Hamiltonian tool to bolster x-ray crystallography in the context of the method steps described above, the invention embraces any "force-field assessment" add-on to bolster x-ray crystallography in the manner described above, and with the present scoring and real-world evaluation approach. By "force-field assessment" in this context is meant any energy functional or potential energy functional method from either the quantum mechanics or molecular mechanics disciplines. Therefore, although the invention has been specifically disclosed and described above, the legal scope of the invention is only to be construed insofar as is set forth in the accompanying claims.

TABLE 1

Scoring results for possible tautomeric structures of the ligand AZM in PDB 3HS4

| Structure-3HS4 | SE | RSCC | ZDD | XModeScore |
|---|---|---|---|---|
| 3 | 5.55 | 0.989 | 12.8 | 2.72 |
| 2 | 8.89 | 0.978 | 24.9 | −0.74 |
| 1 | 10.8 | 0.975 | 27.2 | −1.98 |
| Resolution 1.4Å | | | | |
| 3 | 5.89 | 0.989 | 9.42 | 2.77 |
| 2 | 9.31 | 0.981 | 18.1 | −0.88 |
| 1 | 10.1 | 0.978 | 20.9 | −1.88 |
| Resolution 1.6 Å | | | | |
| 3 | 6.01 | 0.987 | 7.87 | 2.72 |
| 2 | 8.71 | 0.98 | 14.3 | −0.70 |
| 1 | 9.75 | 0.978 | 16.8 | −2.02 |
| Resolution 1.8 Å | | | | |
| 3 | 6.13 | 0.988 | 6.18 | 2.13 |
| 2 | 6.46 | 0.982 | 11.4 | 0.40 |
| 1 | 9.24 | 0.978 | 14.6 | −2.53 |
| Resolution 2.0 Å | | | | |
| 3 | 5.58 | 0.989 | 6.56 | 2.68 |
| 2 | 8.74 | 0.982 | 12.3 | −1.24 |
| 1 | 7.86 | 0.975 | 15.6 | −1.45 |
| Resolution 2.2 Å | | | | |
| 3 | 5.77 | 0.989 | 6.17 | 2.77 |
| 2 | 7.73 | 0.981 | 10.8 | −1.31 |
| 1 | 8.35 | 0.984 | 10 | −1.47 |
| Resolution 2.5 Å | | | | |
| 3 | 5.4 | 0.989 | 7.65 | 2.47 |
| 2 | 8.2 | 0.986 | 8.62 | −0.04 |
| 1 | 11.1 | 0.984 | 9.48 | −2.43 |
| Resolution 2.8 Å | | | | |
| 3 | 5.45 | 0.984 | 9.67 | 2.8 |
| 2 | 8.25 | 0.984 | 10.2 | −1.39 |
| 1 | 8.74 | 0.982 | 10.1 | −1.41 |
| Resolution 3.0 Å | | | | |
| 2 | 8.02 | 0.983 | 11.3 | 0.49 |
| 3 | 5.67 | 0.981 | 11.9 | 0.01 |
| 1 | 8.61 | 0.983 | 11.5 | −0.50 |

TABLE 2

Geometry and electron density characteristics
(ZDD-/+) of the atom N1 of AZM
directly bound to the Zn atom in the structure 3HS4.

| 3HS4: AZM tautomers | 1 | 2 | 3 |
|---|---|---|---|
| Zn-N1$^{AZM}$, Å | 2.05 | 2.07 | 1.90 |
| N1$^{AZM}$: ZDD-/+ | 14.27/20.45 | 14.58/21.64 | 4.35/4.66 |

TABLE 3

Scoring results for possible protonated states
of ASP215 in PDB 2JJJ

| Structure-2JJJ | SE | RSCC | ZDD | XModeScore |
|---|---|---|---|---|
| 1 | 12.2 | 0.987 | 6.05 | 139 |
| 2 | 9.08 | 0.977 | 12.3 | 0.24 |
| 3 | 17.3 | 0.979 | 11.3 | −1.83 |
| Resolution 1.4 Å | | | | |
| 1 | 12.7 | 0.99 | 3.66 | 1.33 |
| 2 | 9.26 | 0.983 | 7.19 | −0.08 |
| 3 | 17.3 | 0.987 | 5.36 | −1.25 |
| Resolution 1.6 Å | | | | |
| 1 | 12.7 | 0.988 | 3.26 | 1.43 |
| 2 | 9.29 | 0.98 | 6.15 | 0.01 |
| 3 | 17.5 | 0.983 | 4.98 | −1.44 |
| Resolution 1.8 Å | | | | |
| 1 | 12.9 | 0.989 | 2.66 | 1.09 |
| 2 | 9.29 | 0.981 | 6.52 | −0.19 |
| 3 | 17.5 | 0.987 | 3.68 | −0.90 |
| Resolution 2.0 Å | | | | |
| 1 | 12.6 | 0.989 | 1.87 | 1.13 |
| 2 | 9.24 | 0.982 | 4.94 | −0.23 |
| 3 | 17.5 | 0.987 | 2.64 | −0.90 |
| Resolution 2.2 Å | | | | |
| 1 | 12.4 | 0.986 | 2.92 | 0.97 |
| 2 | 9.24 | 0.981 | 5.36 | −0.28 |
| 3 | 17.4 | 0.987 | 3.10 | −0.68 |
| Resolution 2.5 Å | | | | |
| 1 | 12.8 | 0.988 | 1.35 | 0.98 |
| 2 | 9.48 | 0.986 | 2.38 | −0.28 |
| 3 | 17.9 | 0.989 | 1.46 | −0.71 |
| Resolution 2.8 Å | | | | |
| 2 | 9.52 | 0.987 | 1.9 | 0.03 |
| 3 | 17.9 | 0.991 | 0.186 | 0.02 |
| 1 | 13.1 | 0.99 | 1.23 | −0.06 |

TABLE 4

Selected interatomic distances and electron
density characteristics (atomic ZDD-/+) for
atoms of the catalytic residue Asp215 in 2JJJ.

| 2JJJ: Asp215 states | 1 | 2 | 3 |
|---|---|---|---|
| OD2$^{Asp215}$-F2$^{0Qs}$, Å | 2.88 | 2.74 | 3,02 |
| OD2$^{Asp215}$-OH2$^{0Qs}$, Å | 2.65 | 2.64 | 2.73 |
| OD1$^{Asp215}$-OH2$^{Asp32}$, Å | 2.90 | 2.88 | 3.00 |
| OD1$^{Asp215}$: ZDD-/+ | 5.98/3.76 | 7.20/5.09 | 7.78/5.35 |
| OD2$^{Asp215}$: ZDD-/+ | 3.66/1.23 | 10.96/7.79 | 12.89/8.10 |

We claim:

1. An analytic method more efficiently to identify conformational, protonation, or solvent effect information from a real world molecule of interest by using low resolution x-ray crystallography, comprising the steps of: a) selecting an aliquot of a real world molecule sample as a molecule to be diagnosed; b) imaging said molecule by low resolution x-ray crystallography and collecting a quantity of crystallography data generated thereby; c) assaying x-ray density within said crystallography data and creating from said crystallography data thus assayed a population set containing a plurality of set elements consisting of one or more of conformational, protonation or solvent effect information of said real world molecule; d) determining a local ligand strain energy value SE for each of said elements; e) determining ZDD for each of said elements by calculating a real-space difference density Z for each element and compiling ZDD data therefrom; and f) selecting a single element from among said elements that represents the true conformational, protonation or solvent effect information for at least one moiety of said molecule by calculating Score$_i$ according to the following equation, $$\text{Score}_i = \{((ZDD_i - \mu_{ZDD})/\sigma_{ZDD}) + ((SE_i - \sigma_{SE})/\sigma_{SE})\}$$

wherein the highest Score$_i$ obtained for said population corresponds to the best conformational, protonation or solvent effect form "i" that fits both SE and ZDD criteria, so that Score$_i$ when output to a user identifies the element from said population that most closely corresponds with said real world molecule thus diagnosed with increased time efficiency using said low resolution x-ray crystallography compared to the same method using atomic resolution x-ray crystallography.

2. An analytic method to identify conformational, protonation, or solvent effect information from a real world molecule of interest by using low resolution x-ray crystallography having a maximum resolution of 1.1 angstrom, comprising the steps of: a) selecting an aliquot of a real world molecule sample as a molecule to be diagnosed; b) imaging said molecule by low resolution x-ray crystallography and collecting a quantity of crystallography data generated thereby; c) assaying x-ray density within said crystallography data and creating from said crystallography data thus assayed a population set containing a plurality of set elements consisting of one or more of conformational, protonation or solvent effect information of said real world molecule; d) determining a local ligand strain energy value SE for each of said elements; e) determining ZDD for each of said elements by calculating a real-space difference density Z for each element and compiling ZDD data therefrom; and f) selecting a single element from among said elements that represents the true conformational, protonation or solvent effect information for at least one moiety of said molecule by calculating Score$_i$ according to the following equation, $$\text{Score}_i = \{((ZDD_i - \mu_{ZDD})/\sigma_{ZDD}) + ((SE_i - \sigma_{SE})/\sigma_{SE})\}$$

wherein the highest Score$_i$ obtained for said population corresponds to the best conformational, protonation or solvent effect form "i" that fits both SE and ZDD criteria, so that Score$_i$ when output to a user identifies the element from said population that most closely corresponds with said real world molecule thus diagnosed with increased time efficiency using said low resolution x-ray crystallography compared to the same method using atomic resolution x-ray crystallography.

3. The method of claim 1, wherein said molecule further is a molecular ligand.

4. The method of claim 3, wherein said ligand is a drug candidate ligand.

* * * * *